United States Patent
Hess et al.

(10) Patent No.: US 9,417,191 B2
(45) Date of Patent: *Aug. 16, 2016

(54) USING REFLECTED AND TRANSMISSION MAPS TO DETECT RETICLE DEGRADATION

(71) Applicant: KLA-Tencor Corporation, Milpitas, CA (US)

(72) Inventors: Carl E. Hess, Los Altos, CA (US); Rui-fang Shi, Cupertino, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/381,304

(22) PCT Filed: Mar. 7, 2013

(86) PCT No.: PCT/US2013/029587
§ 371 (c)(1),
(2) Date: Aug. 27, 2014

(87) PCT Pub. No.: WO2013/142079
PCT Pub. Date: Sep. 26, 2013

(65) Prior Publication Data
US 2015/0103351 A1    Apr. 16, 2015

Related U.S. Application Data

(60) Provisional application No. 61/613,181, filed on Mar. 20, 2012.

(51) Int. Cl.
*G01N 21/00* (2006.01)
*G01N 21/95* (2006.01)
(Continued)

(52) U.S. Cl.
CPC .............. *G01N 21/95* (2013.01); *G01M 11/00* (2013.01); *G01N 21/95607* (2013.01);
(Continued)

(58) Field of Classification Search
CPC .............. G01N 21/95; G01N 21/9501; G01N 2021/9511; G01N 2201/06113; G01N 2201/062; G01N 2201/10; G01M 11/00
USPC ........................................... 356/237.1–237.5
See application file for complete search history.

(56) References Cited

U.S. PATENT DOCUMENTS 6,614,520 B1    9/2003    Bareket et al.
7,069,155 B1    6/2006    Phan et al.
(Continued)

FOREIGN PATENT DOCUMENTS

CN    1266281 A    9/2000
CN    1637622 A    7/2005
(Continued)

OTHER PUBLICATIONS

"International Application Serial No. PCT/US2013/026224, Search Report and Written Opinion mailed Jun. 3, 2013", 11 pgs.
(Continued)

*Primary Examiner* — Hoa Pham
(74) *Attorney, Agent, or Firm* — Kwan & Olynick LLP (57) ABSTRACT

An optical reticle inspection tool is used during an inspection to obtain, for each local area, an average of multiple reflected intensity values corresponding to light reflected from a plurality of sub-areas of each local area of the reticle. The optical reticle inspection tool is also used during the inspection to obtain, for each local area, an average of multiple transmitted intensity values corresponding to light transmitted through the sub-areas of each local area of the reticle. A combined intensity map is generated by combining, for each local area, the average of multiple reflected intensity values and the average of multiple transmitted intensity values such that a reticle pattern of the reticle is cancelled from the combined intensity map if the reticle has not degraded and such that the reticle pattern of the reticle is not cancelled out of the combined intensity map if the reticle has degraded.

22 Claims, 9 Drawing Sheets

(51) Int. Cl.
*G03F 1/84* (2012.01)
*G01M 11/00* (2006.01)
*G01N 21/956* (2006.01)

(52) U.S. Cl.
CPC .......... *G03F 1/84* (2013.01); *G01N 2021/9511* (2013.01); *G01N 2021/95676* (2013.01); *G01N 2201/062* (2013.01); *G01N 2201/06113* (2013.01); *G01N 2201/10* (2013.01)

(56) References Cited

U.S. PATENT DOCUMENTS

| | | | |
|---|---|---|---|
| 7,126,681 B1 * | 10/2006 | Chen | G01N 21/9501 356/237.4 |
| 7,564,545 B2 | 7/2009 | Stokowski | |
| 2002/0085297 A1 | 7/2002 | Boettiger et al. | |
| 2002/0131052 A1 | 9/2002 | Emery | |
| 2003/0174876 A1 | 9/2003 | Eran et al. | |
| 2005/0002020 A1 | 1/2005 | Inoue et al. | |
| 2005/0166171 A1 | 7/2005 | Bartov | |
| 2005/0174570 A1 | 8/2005 | Kvamme et al. | |
| 2008/0304056 A1 | 12/2008 | Alles et al. | |
| 2009/0037134 A1 | 2/2009 | Kulkarni et al. | |
| 2009/0226076 A1 | 9/2009 | Sakai et al. | |
| 2011/0014577 A1 | 1/2011 | Hashimoto | |
| 2011/0235905 A1 | 9/2011 | Yokokawa | |
| 2012/0002860 A1 | 1/2012 | Sakai et al. | |
| 2013/0211736 A1 | 8/2013 | Hess et al. | |
| 2014/0168418 A1 | 6/2014 | Hess | |

FOREIGN PATENT DOCUMENTS

| | | |
|---|---|---|
| JP | 10002863 A | 1/1998 |
| JP | H10170240 A | 6/1998 |
| JP | 2004271421 A | 9/2004 |
| JP | 2005300884 A | 10/2005 |
| JP | 2006018054 A | 1/2006 |
| JP | 2006080437 A | 3/2006 |
| JP | 4822103 B2 | 11/2011 |
| WO | 2011035946 A1 | 3/2011 |
| WO | 2013142079 A1 | 9/2013 |

OTHER PUBLICATIONS

"International Application Serial No. PCT/US2013/074841, Search Report and Written Opinion mailed Sep. 25, 2014", 12 pgs.

"Int'l Application Serial No. PCT/US2013/029587, Preliminary Report on Patentability mailed Oct. 2, 2014", 8 pgs.

Sagiv, Amir et al., "IntenCD: Mask Critical Dimension Variation Mapping", Proc. of SPIE vol. 7028, 70282X, Retrieved from the Internet: < http://proceedings.spiedigitallibrary.org/ on Jan. 14, 2013 Terms of Use: http://spiedl.org/terms >, Accessed on Jan. 14, 2013, 2008, 12 pgs.

"Int'l Application Serial No. PCT/US2013/029587, Search Report and Written Opinion mailed Jun. 24, 2013", 11 pgs.

"U.S. Appl. No. 13/757,103, Non Final Office Action mailed Dec. 21, 2015", 26 pgs.

"U.S. Appl. No. 14/101,712, Examiner Interview Summary mailed Dec. 18, 2015", 1 pg.

"U.S. Appl. No. 14/101,712, Notice of Allowance mailed Dec. 18, 2015", 10 pgs.

"European Application Serial No. 13763512.4, Supplementary Search Report and Search Opinion mailed Nov. 23, 2015", 6 pgs.

Chinese Application Serial No. 201380025799.3, Office Action mailed Apr. 11, 2016, 27 pgs.

* cited by examiner

USING REFLECTED AND TRANSMISSION MAPS TO DETECT RETICLE DEGRADATION

CROSS-REFERENCE TO RELATED APPLICATIONS

This application is a U.S. national application under 5 U.S.C. 371 of PCT Application Number PCT/US13/29587, entitled USING REFLECTED AND TRANSMISSION MAPS TO DETECT RETICLE DEGRADATION, filed 7 Mar. 2013 by Carl E. Hess et al., which claims priority of U.S. Provisional Patent Application No. 61/613,181, filed Mar. 20, 2012, titled "USING TRANSMISSION AND REFLECTED INTENSITY MAPS TO DETECT MASK DEGRADATION" by Carl E. Hess et al. Both applications are herein incorporated by reference in their entireties for all purposes.

TECHNICAL FIELD OF THE INVENTION

The invention generally relates to the field of reticle inspection. More particularly the present invention relates to a method to detect reticle degradation.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

An integrated circuit is typically fabricated from a plurality of reticles. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device. The reticle writer uses the circuit pattern data to write (e.g., typically, an electron beam writer or laser scanner is used to expose a reticle pattern) a plurality of reticles that will later be used to fabricate the particular IC design.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication processes.

After fabrication of each reticle or group of reticles, each new reticle typically is free of defects or degradation. However, the reticle may become defective or degrade after use. Thus, there is a continuing need for improved reticle inspection techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting a photolithographic reticle is disclosed. A plurality of local areas of a reticle is defined. An optical reticle inspection tool is used during an inspection to obtain, for each local area, an average of multiple reflected intensity values corresponding to light reflected from a plurality of sub-areas of each local area of the reticle. The optical reticle inspection tool is also used during the inspection to obtain, for each local area, an average of multiple transmitted intensity values corresponding to light transmitted through the plurality of sub-areas of each local area of the reticle. A combined intensity map is generated by combining, for each local area, the average of multiple reflected intensity values and the average of multiple transmitted intensity values such that a reticle pattern of the reticle is cancelled out of the combined intensity map if the reticle has not degraded and such that the reticle pattern of the reticle is not cancelled out of the combined intensity map if the reticle has degraded.

In a specific implementation, the combined intensity map indicates that the reticle has degraded in a spatially radial pattern that results in the combined intensity map comprising a plurality of intensity values, which correspond to both a reticle pattern portion and a spatially radial pattern of degradation on the reticle, that differs from a plurality of intensity values, which correspond to portions of the reticle that are outside the reticle pattern portion. In a further aspect, the inspection is performed after the reticle is used repeatedly in a photolithography process and the spatially radial pattern is caused by the photolithography process. In yet another embodiment, the average of multiple reflected intensity values and the average of multiple transmitted intensity values are combined so that the combined intensity map comprises a plurality of intensity values, which correspond to pattern portions on the reticle, that are substantially equal to a plurality of intensity values, which correspond to non-pattern portions on the reticle, when there is no degradation on such reticle.

In another embodiment, the average of multiple reflected intensity values for each local area is obtained from a reflected intensity image obtained by the optical reticle inspection tool and the average of multiple transmitted intensity values for each local area is obtained from a transmitted intensity image obtained by the optical reticle inspection tool. In this aspect, the combined intensity map is in the form of an image that combines both the reflected and transmitted intensity images. In a further aspect, each local region corresponds to a pixel of the reflected and transmitted intensity image. In another aspect, each local region corresponds to a patch of the reflected and transmitted intensity image, wherein each patch has a plurality of pixels.

In yet another implementation, the average of multiple reflected intensity values and the average of multiple transmitted intensity values are combined by weighting particular values from the multiple reflected and transmitted intensity values. In another aspect, the plurality of local areas substantially comprises the entire active area of the reticle and the combined intensity map is generated for the entire active area of the reticle. In another embodiment, the inspection is performed while a pellicle is mounted on the reticle and the combined intensity map indicates whether a pellicle of the reticle has degraded over time more than a predefined level.

In certain embodiments, the invention pertains to an inspection system for inspecting a photolithographic reticle for inspecting a photolithographic reticle. The system includes a light source for generating an incident beam and an illumination optics module for directing the incident beam onto a sample. The system also has a collection optics module for directing a reflected output beam, which is reflected from the sample in response to the incident beam, and a transmitted output beam, which is transmitted through the sample in response to the incident beam, to at least one sensor. At least one sensor is configured for detecting the reflected output beam and generating a reflected intensity image or signal for the reflected output beam and detecting the transmitted output beam and generating a transmitted intensity image or signal for the transmitted output beam. The system further includes a controller that is configured to perform at least some of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations or apparatus components have not been described in detail to not unnecessarily obscure the present invention. While the invention will be described in conjunction with the specific embodiments, it will be understood that it is not intended to limit the invention to the embodiments.

The terms "reticle" generally includes a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material.

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, and a chromeless phase lithography PSM. A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs). If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

A reticle may become damaged over time in a number of different ways. In a first degradation example, the photolithographic exposure process may result in physical degradation of the opaque material of the reticle. For instance, a high power beam, such as a high powered deep ultra violet (UV) beam at 193 nm, that is used on the reticle may physically cause damage to the opaque material on the reticle. Damage may also be caused by other wavelengths, such as a 248 nm UV beam. In effect, the UV beam can physically cause the opaque patterns on the reticle to slump by blasting the corners off of opaque features and causing the features to flatten. This particular physical effect can adversely affect the critical dimensions (CD's) of the reticle.

Figure 1A:
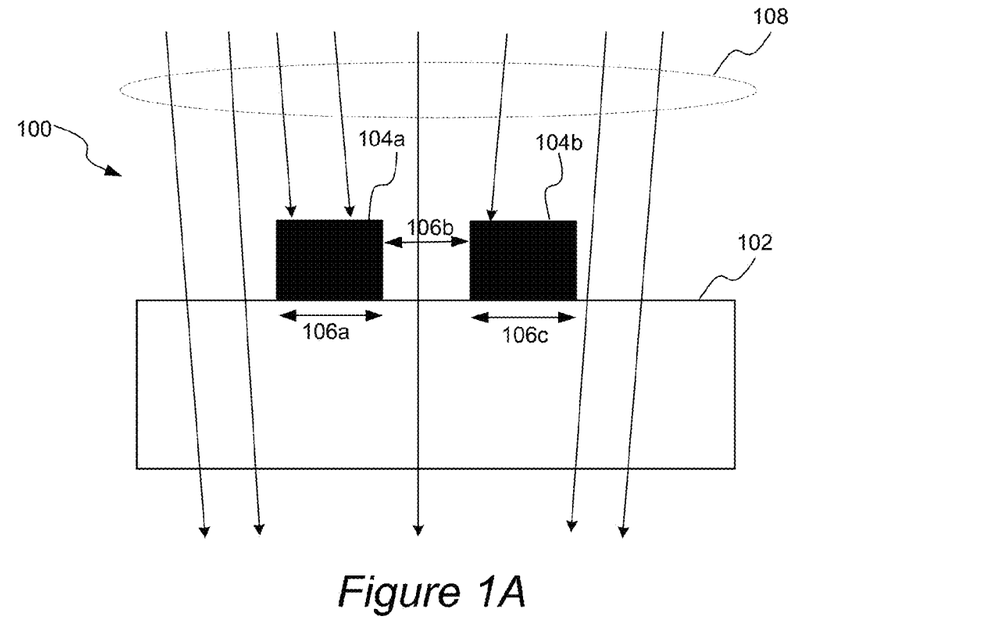
FIG. 1A is a diagrammatic side view of a reticle portion undergoing photolithographic exposure using a high power, deep ultra violet (UV) light.

FIG. 1A is a diagrammatic side view of a reticle portion 100 undergoing photolithographic exposure using a high power, deep ultra violet (UV) light 108. The reticle portion 100 includes opaque patterns 104a and 104b formed on transparent substrate 102. The opaque portions 104a and 104b substantially block the light 108, while the transparent portions pass the light 108 to the underlying wafer (not shown) to expose a photolithography film on such wafer that reacts to the incident light 108. The exposed regions of the film form a pattern on the wafer after further processing, such as an etching process to remove the exposed (or unexposed) film portions.

As shown, the opaque pattern structures 104a and 104b are designed and formed with critical dimension (CD) widths 106a and 106c, respectively. Similarly, the spacing between opaque features 104a and 104b has CD width 106b. A particular CD value may generally affect how such particular reticle feature is transferred to the wafer in the photolithography process and such CD is chosen to optimize this transfer process. Said in another way, if a certain reticle feature's CD value is within a specified CD range, such CD value will result in fabrication of a corresponding wafer feature that allows proper operation of the resulting integrated circuit as intended by the circuit designer. Features are typically formed with minimum dimensions that also result in operational circuits so as to conserve integrated chip area.

During each exposure, deep UV light is applied to the reticle at relatively high power. The UV beam can cause the surface of the opaque features to bubble and distort, producing a roughened surface (not shown). After this roughening effect, the high power UV light tends to "push down" the opaque features, resulting in more rounded and flattened opaque features. The mask feature dimensions, e.g., 106a-c of FIG. 1A, may initially have CD values that meet predefined specifications. However, after repeated exposure to deep UV, for example, the mask features may degrade such that CD values are no longer within the predefined specifications. This type of degradation is referred to as "chrome" degradation since this type of problem typically occurs in chrome type reticles.

Figure 1B:
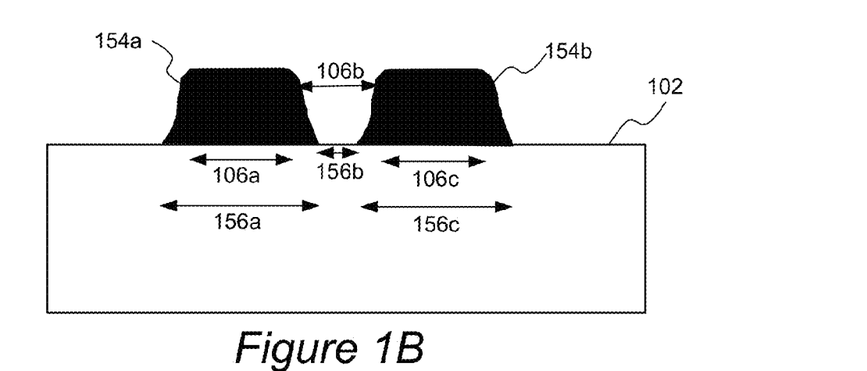
FIG. 1B is a diagrammatic side view of the reticle of FIG. 1A illustrating degradation of mask features due to repeated lithographic exposure.

FIG. 1B is a diagrammatic side view of the reticle of FIG. 1A illustrating a physical type degradation of the mask features due to repeated lithographic exposure. As shown, degraded features 154a and 154b show significantly altered dimensions 156a and 156c, as well as affecting the spacing width 156b. As shown, opaque features 154a and 154b have significantly larger widths 156a and 156c, as compared to original widths 106a and 106c, respectively, while the spacing between such opaque features has a much smaller width 156b, as compared with the original width 106b. As a result of this degradation, the feature CD values may have significantly changed so as to affect wafer yield. For instance, mask feature widths 156a and 156c may be significantly larger than the original line width CD, while the spacing width 156b may be significantly smaller than the original line spacing width CD.

Figure 1C:
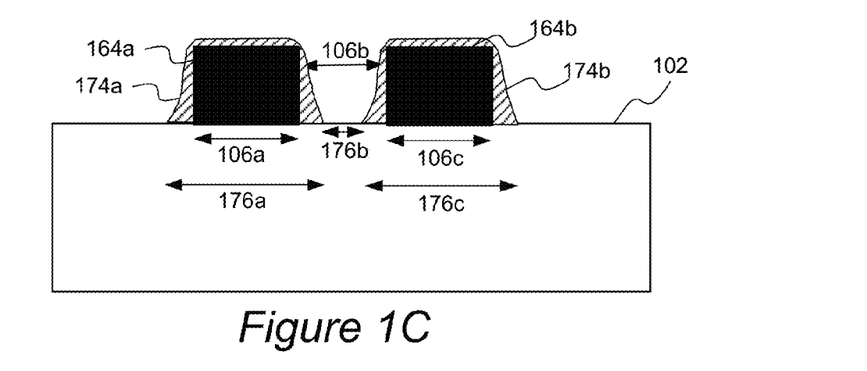
FIG. 1C illustrates degradation of a MoSi reticle portion that occurred during repeated photolithography exposure processes.

Another type of degradation occurs with MoSi reticles, in particular, but may also occur in other types of reticles. FIG. 1C illustrates degradation of a MoSi reticle portion that occurred during repeated photolithography exposure processes. During exposure, the light chemically reacts with the MoSi features 164a and 164b so as to cause an oxidation layer 174b and 174b to be formed on such MoSi features. That is, the light causes a photo-catalyzed chemical reaction so as to ionize oxygen from the MoSi material and cause oxidation of the surface of such MoSi features. This oxidation causes the opaque MoSi features to become rounded by an oxidation build-up along the edges. This MoSi oxidation also causes the CD's to change. For instance, MoSi features 164a and 164b, along with extra oxidation material 174a and 174b, result in larger feature widths CD of 176a and 176c, respectively, and a smaller spacing CD 176b.

Figure 2:
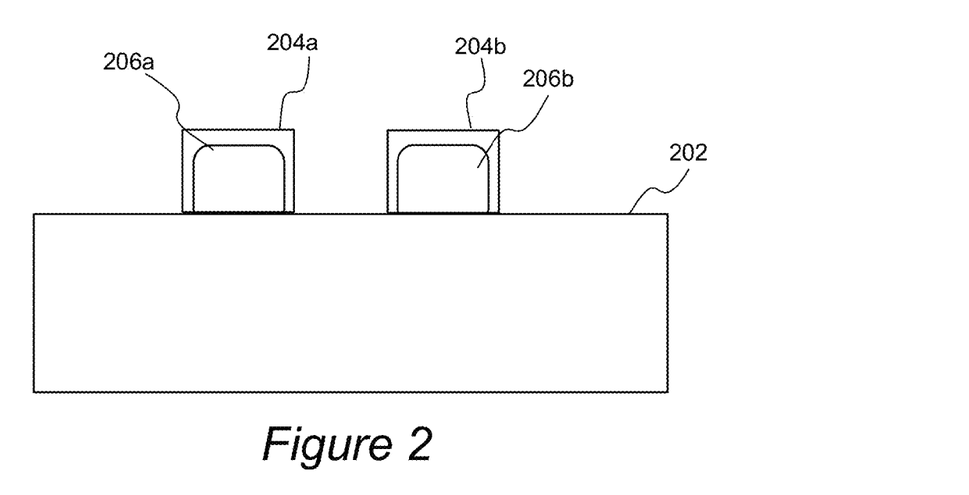
FIG. 2 illustrates erosion of reticle features due to a cleaning process.

In another degradation example, the opaque features may be made smaller by a cleaning process. Chemical contaminants from the air or other sources may be formed on the reticle surface to cause a "haze." This haze is typically cleaned off of the reticle. However, this cleaning process may cause erosion of the reticle features. FIG. 2 illustrates erosion of reticle features due to a cleaning process. Before cleaning, the reticle includes reticle features 204a and 204b of a particular size and shape on transparent substrate 202. During cleaning, the cleaning solution may cause these reticle features to erode to form eroded features 206a and 206b. Cleaning type degradation may also affect the wafer yield, especially as CD becomes smaller and smaller (e.g., 200 nm or lower).

Figure 3A:
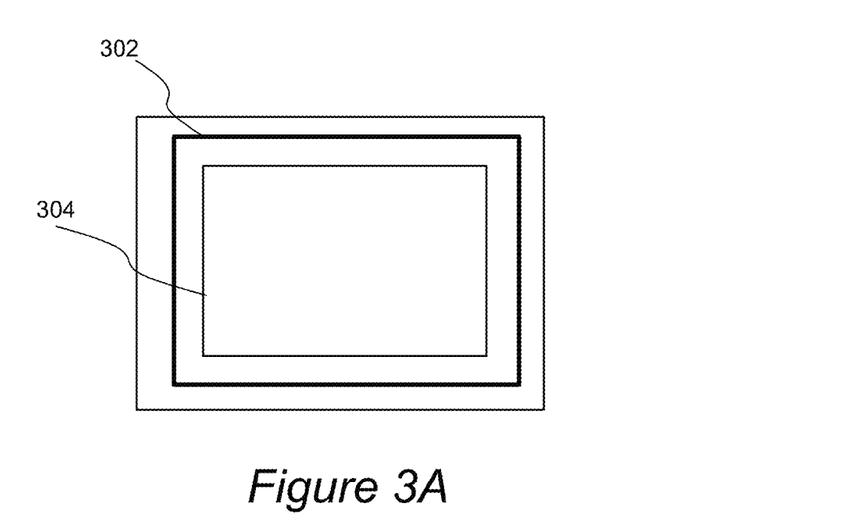
FIG. 3A is a top diagrammatic view of a reticle having an active region surrounded by a pellicle frame.
Figure 3B:
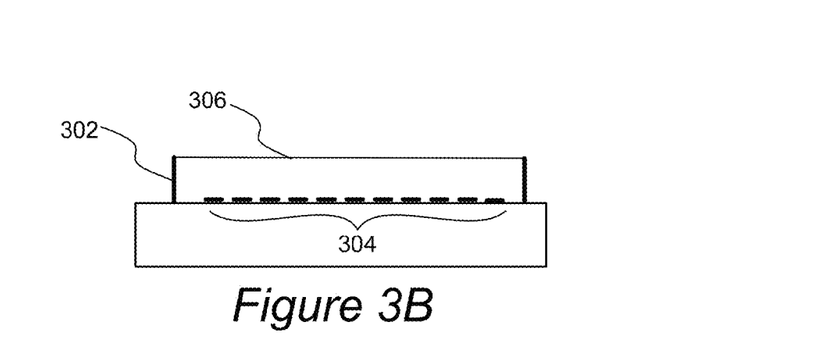
FIG. 3B shows a diagrammatic side view of the reticle and pellicle of FIG. 3A.

The pellicle of a reticle may also degrade over time. FIG. 3A is a top diagrammatic view of a reticle having an active region 304 surrounded by a pellicle frame 302. FIG. 3B shows a diagrammatic side view of the reticle and pellicle of FIG. 3A. The pellicle includes the pellicle frame 302 and a transparent film 306 supported by the pellicle frame 302. The pellicle is mounted on the reticle to protect the active region 304 from contamination.

Since the lithography system has a relatively high numerical aperture, small contaminants on the back of the reticle are not in focus and do not usually affect the exposure characteristics. However, the pellicle film may darken or otherwise change over time during exposure. Although the pellicle film 306 may be replaced with a new film, for example, after a cleaning process, it would be beneficial to monitor pellicle degradation in between cleanings. Pellicle degradation tends to be radial over time and may adversely affect wafer fabrication.

Certain embodiments provide techniques and systems for detecting the degradation of a reticle, such as chrome, MoSi, pellicle, or cleaning type degradations, using a combination of reflection and transmission intensity maps obtained for the sample, e.g., reticle. Degradation tends to result in a spatially varying signature across a combined map, and this signature gets progressively more pronounced with repeated photolithography exposures.

Figure 4:
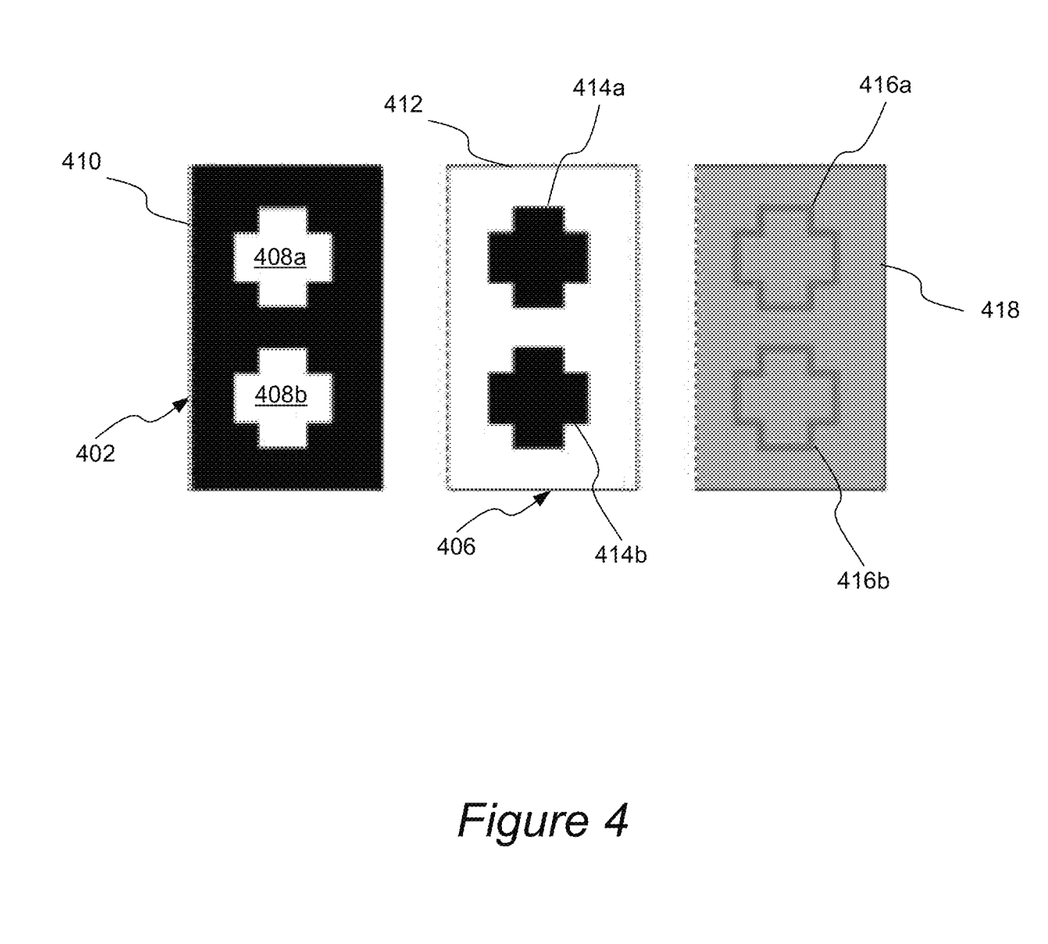
FIG. 4 is a diagrammatic representation of a combined intensity map obtained from a simple opaque pattern on a reticle in accordance with one embodiment of the present invention.

FIG. 4 is a diagrammatic representation of a combined intensity map 418 obtained from a simple reticle pattern in accordance with one embodiment of the present invention. As shown, a reflected image 402 of a reticle area containing a simple two cross pattern is obtained. The reflected image 402 will tend to have dark area 410 that corresponds to the transparent reticle regions since the light passes through the transparent portion of the reticle and is not reflected back to the detector. In contrast, the reflected image 402 will exhibit brighter areas 408a and 408b for the two opaque reticle cross-shaped patterns from which light is reflected back to the detector.

The corresponding transmitted image 406 will tend to have an opposite intensity pattern than the reflected image 402. As shown, the transmitted image 406 includes dark cross portions 414a and 414b for the opaque reticle pattern and bright area 412 for the transparent reticle portion.

A combined image 418 can be formed from the reflected and transmitted images. For instance, averaging the reflected and transmitted images together results in a relatively grey combined image 418. That is, most of the opaque reticle pattern will be cancelled out of the combined image, except for the pattern edges 416a and 416b. Although the cancellation of the reticle pattern from the combined image is imperfect, a broad area average can result in a dramatic reduction in the pattern impact for the combined intensity map.

When the impact from the reticle pattern is minimized, degradation can be easily seen in the combined map. For example, chrome degradation will tend to result in an imbalanced impact in the reflected image, as compared to the transmitted image. Chrome degradation can cause a significant decrease in reflectivity of the opaque reticle material without a corresponding change in the transmitted image. This imbalance can then be highlighted in the combined map since the reticle pattern is not cancelled out as well in the degraded reticle portions.

Figure 5:
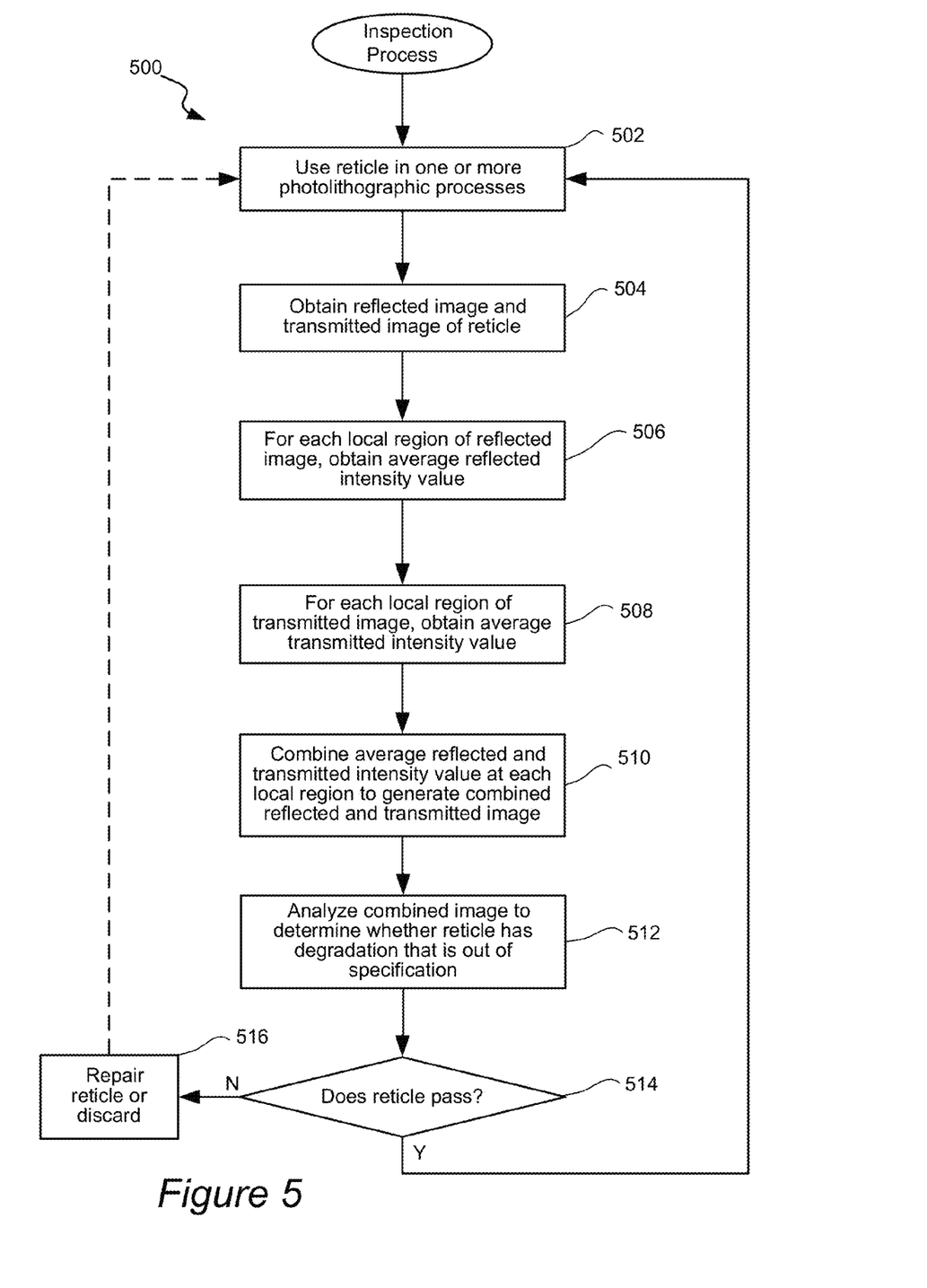
FIG. 5 is a flow chart illustrating a reticle inspection process in accordance with one embodiment of the present invention.

FIG. 5 is a flow chart illustrating a reticle inspection process 500 in accordance with one embodiment of the present invention. After a reticle is fabricated, such reticle can be used in one or more photolithography processes in operation 502. However, the reticle does not have to be used prior to being inspected. Regardless of whether the reticle is used, a reflected and transmitted image of the reticle may be obtained in operation 504.

An average reflected intensity value for each local region of the reflected image may then be obtained in operation 506. Likewise, an average transmitted intensity value for each local region of the transmitted image may also be obtained in operation 508. Each reticle image can generally be divided into a plurality of local regions from which multiple intensity values from multiple points are obtained. In one example, each local region corresponds to a pixel. In another example, each local region corresponds to a patch portion, which includes a plurality of pixels. In the following example, patch portions are used although any suitable type and size of local area can be utilized with techniques of the present invention.

Patch portions of the reticle can be scanned to obtain this intensity data. The patch portions may be any size and shape, depending on the particular system and application requirements. In general, multiple intensity values for each patch portion may be obtained by scanning the reticle in any suitable manner. By way of example, multiple intensity values for each patch portion may be obtained by raster scanning the reticle. Alternatively, the images may be obtained by scanning the reticle with any suitable pattern, such as a circular or spiral pattern. Of course, the sensors (one or more) may have to be arranged differently (e.g., in a circular pattern) and/or the reticle may be moved differently (e.g., rotated) during scanning in order to scan a circular or spiral shape from the reticle.

In the example illustrated below, as the reticle moves past the sensors, light is detected from a rectangular region (herein referred to as a "swath") of the reticle and such detected light is converted into multiple intensity values at multiple points in each patch. In this embodiment, the sensors of the scanner are arranged in a rectangular pattern to receive light that is reflected and transmitted from the reticle and generate therefrom intensity data that corresponds to a swath of patches of the reticle. In a specific example, each swath can be about 1 million pixels wide and about 1000 to 2000 pixels high, while each patch can be about 2000 pixels wide and 1000 pixels high. In one example, each pixel has a size of 72 nm.

Figure 6A:
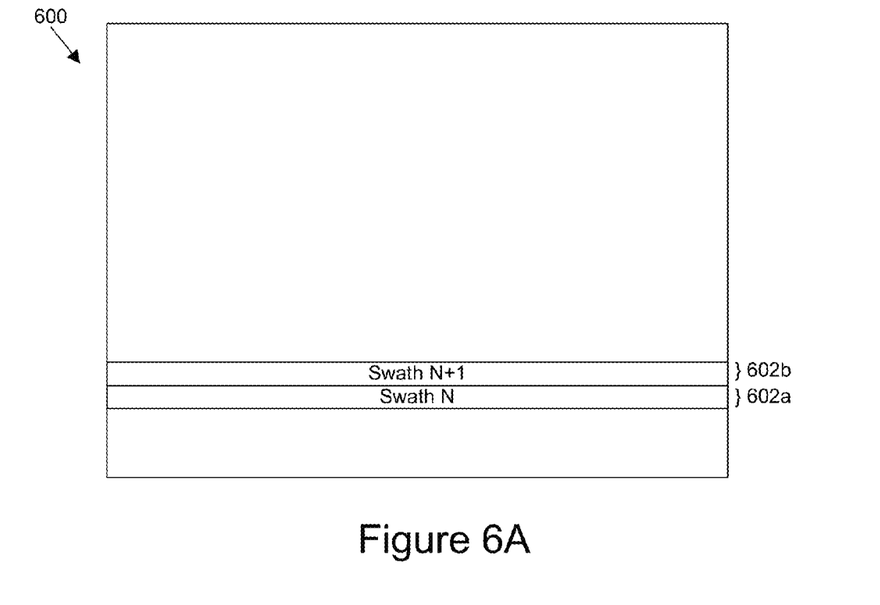
FIG. 6A is a diagrammatic representation of two sets of intensity data corresponding to two "swaths" of a reticle in accordance with embodiment of the present invention.
Figure 6B:
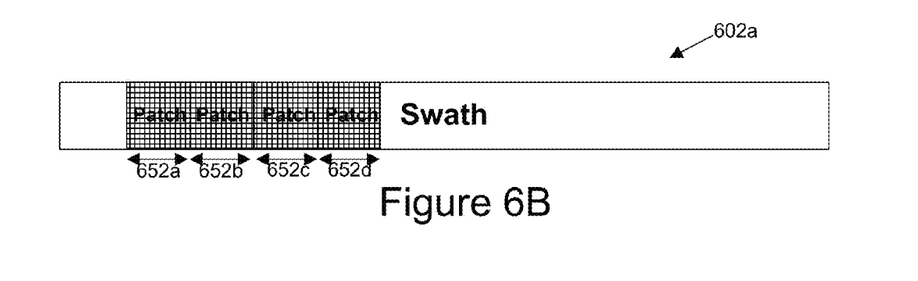
FIG. 6B is a diagrammatic illustration of an intensity data set that corresponds to a swath that is divided into patches in accordance with a specific implementation.

FIG. 6A is a diagrammatic representation of two sets of intensity data, e.g., reflected and transmitted data, corresponding to two "swaths" 602a and 602b of a reticle 600 in accordance with embodiment of the present invention. Each set of intensity data may correspond to a "swath" of the reticle 600. Each set of intensity data may be obtained by sequentially scanning swaths from the reticle in a serpentine or raster pattern. For example, the first swath 602 of the reticle 600 is scanned by an optical beam of an optical inspection system from left to right to obtain a first set of intensity data. The second swath 604 is then scanned from right to left to obtain a second set of intensity data. FIG. 6B is a diagrammatic illustration of the intensity data set 602a, which corresponds to swath that is divided into patches. As shown, the intensity data 602a further includes the intensity data for a plurality of patches, such as such intensity data sets 652a, 652b, 652c, and 652d corresponding to patches of a swath of a reticle.

Figure 6C:
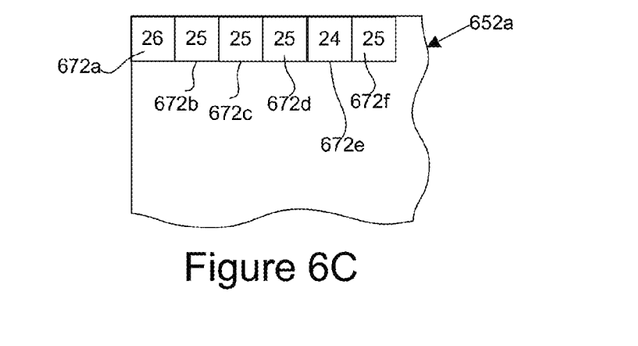
FIG. 6C illustrates multiple intensity values corresponding to multiple pixels or points of a particular patch of a particular swath of a reticle.

During or after intensity data is collected for multiple points in each patch of each swath, an average intensity value may also be determined for each patch or set of one or more patches, for example, of each reflected and transmitted image. FIG. 6C illustrates multiple intensity values (e.g., 672a, 672b, 672c, 672d, 672e, and 672f) corresponding to multiple pixels or points of a particular patch 652a of a particular swath of a reticle. For example, reflected intensity data set 652a corresponding to a patch of the reticle may include reflected intensity values 26, 25, 25, 25, 24, 25, etc. All of the reflected intensity values for each patch may be averaged together to determine an average reflected intensity value (e.g., 25) for such patch.

Reflected and transmitted intensity values for each patch may be obtained using an optical inspection tool that is set up in any suitable manner. For instance, an optical inspection tool is generally set up with a set of operating parameters or a "recipe" for obtaining both reflected and transmitted intensity values. Recipe settings may include one or more of the following settings: a setting for scanning the reticle in a particular pattern, pixel size, a setting for grouping adjacent signals from single signals, a focus setting, an illumination or detection aperture setting, an incident beam angle and wavelength setting, a detector setting, a setting for the amount of reflected or transmitted light, aerial modeling parameters, etc.

Referring back to FIG. 5, the average reflected and transmitted intensity values at each local region (e.g., patch or pixel) may be combined to generate a combined reflected (R) and transmitted (T) image or map in operation 510. For example, the R and T average for each pixel, patch, or each set of patches may be summed or averaged together.

Specific R and/or T values may also be weighted. For example, different R or T intensity values can be weighted differently so that the cancellation of the reticle opaque pattern in the combined image or map is optimized (e.g., minimum reticle pattern remains in the combined image). In one implementation, different R intensity values can be weighted differently so as to maximize pattern cancellation. If a reticle without degradation results in a reflected image having particular intensity values (colors) that correspond to the reticle's pattern portions, these particular R intensity values can be weighted so as to cancel out with the T intensity values that correspond to the same reticle pattern portions.

In some cases, R and T signals for particular regions may have a same sign, instead of an opposite sign, which may indicate that the results are inconsistent in the associated regions and may not be trustworthy. Thus, the combination of R and T could be down-weighted in such regions or removed from the computation if insufficiently trustworthy.

Weight values can be obtained by analysis of the inspection results from a known good reticle that has been verified to have substantially no degradation or defects. A reticle may be verified or defined as having substantially no degradation or defects by any suitable manner. For example, a buyer of a newly manufactured reticle may assume that the reticle has been verified by the manufacturer as free of defects and degradation. Alternatively, the reticle may be inspected with an optical or scanning electron microscope to determine whether there are any CD uniformity defects on the reticle or the reticle has degraded, for example, by performing a die-to-database inspection. A reticle may be similarly inspected after cleaning to remove haze, as well as other types of degradation and defects.

After a combined intensity map is provided, such map may then be analyzed to determine whether the reticle has degradation that is out of specification in operation 512. It may then be determined whether the reticle passes inspection based on such map in operation 514. For instance, a user may determine that the presence of any spatial varying signature on the combined map image represents degradation of the reticle since a reticle that has not degraded will tend to produce a uniform intensity combined image. Alternatively, an automated process may be determine whether any spatial variation has associated average intensity values that are above (or below) a predefined threshold. If an average intensity value is above (or below) the predefined threshold, the corresponding reticle portion may then be more carefully reviewed to determine whether the reticle is defective and can no longer be used. For instance, a SEM may be used to review the defective area to determine whether critical dimensions (CD's) are out of specification.

If the reticle fails inspection, the reticle may be discarded or repaired if possible in operation 516. For instance, certain defects can be cleaned from the reticle. After repair, an inspection may be performed on the reticle at any time and the procedure 500 repeated.

Any suitable mechanism may be used to store and/or display a combined reflected and transmitted intensity map in any suitable form. For example, the intensity map can be represented textually as a list of average intensity variation values for each area of the reticle. Each combined average intensity value may be listed alongside corresponding reticle area coordinates. Each combined intensity value can also be represented by a metric, such as the standard deviation or variance of the grid point difference values. Alternatively or additionally, a combined intensity map may be represented visually so that different intensity variation values or ranges are shown as different visual ways, such as differently colored reticle areas, different bar graph heights, different graph values, or 3-dimensional representations, etc. A combined intensity map can be represented with different grid point sampling sizes or by fits to different functional forms such as a polynomial fit or a Fourier transform. Individual reflected and transmitted maps can also be represented, for example visually or quantitatively.

Figure 7A:
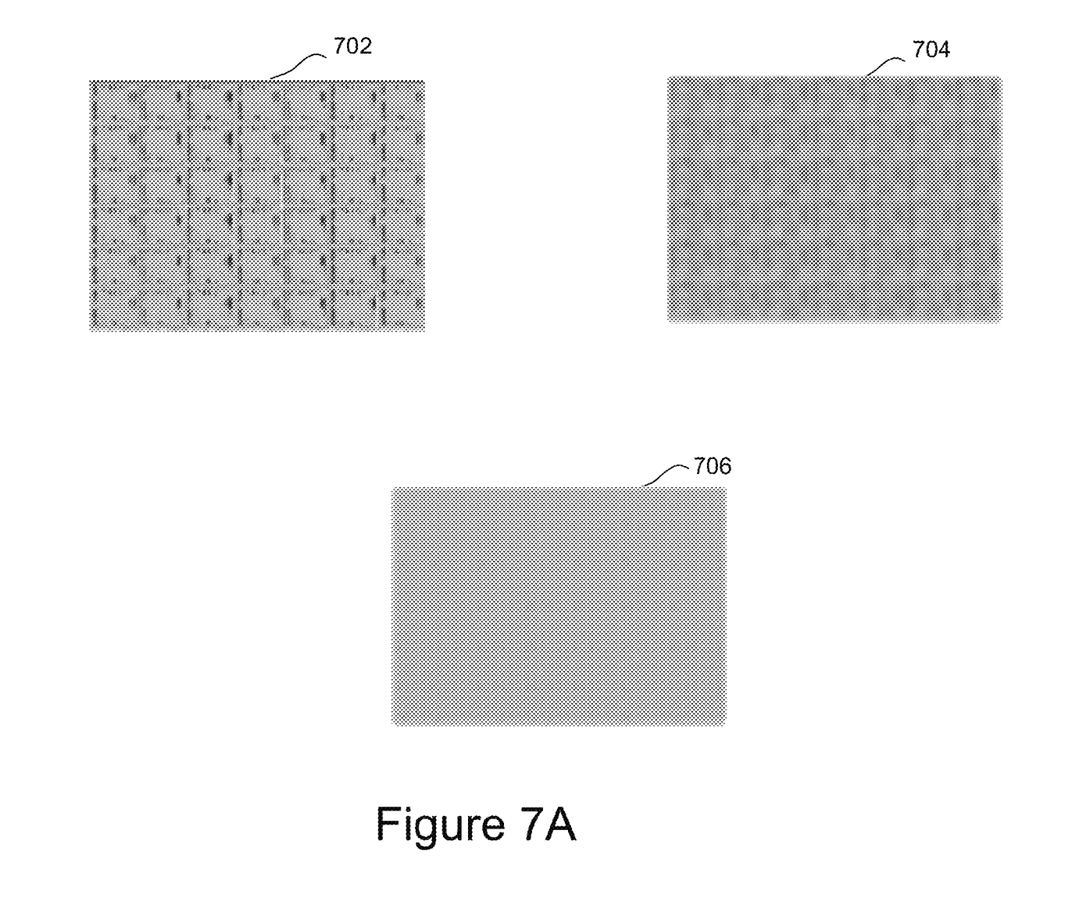
FIG. 7A illustrates the results of combining reflected and transmitted images from a reticle having substantially no degradation in accordance with a specific implementation of the present invention.

When degradation has not yet occurred on a reticle, a combined reflected and transmitted image tends to be mostly gray since the opaque patterns result in opposite intensity values in the reflected and transmitted images. FIG. 7A illustrates the results of combining reflected and transmitted images from a reticle having substantially no degradation in accordance with a specific implementation of the present invention. As shown, a reflected image 702 and transmitted image 704 are combined into a combined image 706 that averages the reflected and transmitted intensity values of each local region. The resulting combined image 706 has a substantially uniform gray appearance.

Figure 7B:
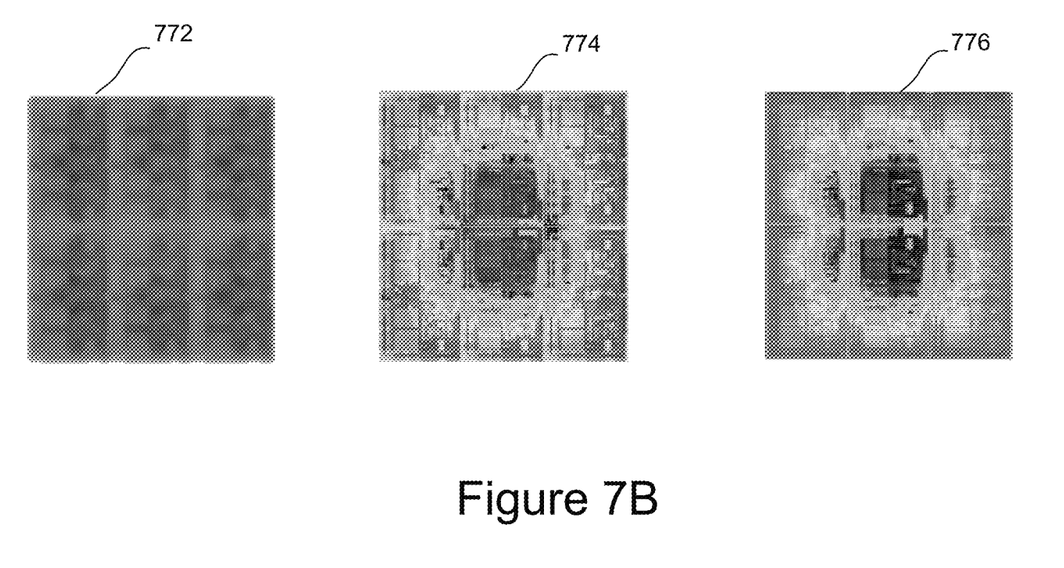
FIG. 7B illustrates the results of combining reflected and transmitted images from a reticle having significant degradation in accordance with a specific implementation of the present invention.

FIG. 7B illustrates the results of combining reflected and transmitted images from a reticle having significant degradation in accordance with a specific implementation of the present invention. As shown, significant degradation shows more in reflected image 774 than transmitted image 772. The resulting combined image 776 shows this substantial radial degradation, as well as areas of the reticle pattern that has not cancelled out of the combined image.

Certain combined intensity map embodiments illustrate intensity changes in a spatial dimension for a reticle. For instance, a combination intensity map corresponds to the average of transmitted and reflected light for specific larger areas of the reticle. This combined intensity map illustrates average spatial variation without having to resolve defects on a fine scale resolution. Additionally, moderate degradation can show in a combined intensity image before such degradation can be clearly seen in the reflected and/or transmitted images. A combined intensity map may also be easily generated and applied to non-repeating reticle features, as well as repeating reticle features.

Certain embodiments of the present invention also may allow a higher number of points to be sampled, as compared to other inspection techniques, for example, as performed with a SEM. Since an SEM inspection is very slow, sparse sampling (e.g., typically not more than 2000 points) is often used. In one example implementation of the present invention, each patch (1 k×2 k) contains about 2 million pixels that are scanned to obtain intensity values for all 2 million points of each pixel. If an average is obtained for each patch, 2 million points are sampled. In another example, averaging the points in 2 patches results in 1 million points being sampled for each 2-patch grid. If 50 patches are averaged, 40,000 points are sampled for each 50-patch grid. Averaging 200 patches results in 10,000 points being sampled, which is still much higher than the maximum number of points one may wish to sample in an SEM inspection.

The intensity values corresponding to the reflected light may be combined with the intensity values for the transmitted light before or after determining the average intensity value for each patch. For instance, an average of the reflected and transmitted intensity values may be determined for each point or pixel. Alternatively, the averages may be calculated separately for the reflected and transmitted intensity values of a patch. The separately calculated reflected average and transmitted average for each patch may then be combined or averaged together. In one example implementation, the reflected (R) and transmitted (T) values may be combined by (T−R)/2. The R and T average values can also be summed. The reflected signal typically is the opposite sign from the transmitted signal. Hence, subtracting the two maps adds the signals together. Since the noise sources are different for T and R, the noise can tend to be averaged out of the combined signal.

A combined intensity map may be generated for the active region of the reticle while the pellicle is attached or after the pellicle is removed (e.g., to be replaced). The active region is the reticle pattern portion that is used to generate corresponding patterns on the wafer during the lithography process. That is the reticle active region is used to generate a plurality of die regions of the wafer. If the pellicle is present, the combined intensity map may show degradation of the reticle active region, pellicle, or both.

The combined intensity map will tend to show only non-uniform degradation. For instance, the intensity difference map may show a radial degradation pattern across the reticle or pellicle. Intensity may vary based on different density levels of the active region. For instance, a same degradation may show more clearly in the combined intensity map in regions corresponding to higher density active regions of the reticle.

The combined intensity map may be generated so as to compensate for pattern density effects. Since the intensity changes are dependent on the number of edge pixels, the intensity value for each patch can be scaled based on the average number of edge pixels. For instance, each particular patch average can be scaled (reduced or increased) by the average number of edge pixels for all of the patches in the reticle divided by the particular patch's number of edge pixels. If a patch has no edges (e.g., empty), this scaling would not be performed for such patch so as to not divide by zero.

Figure 8:
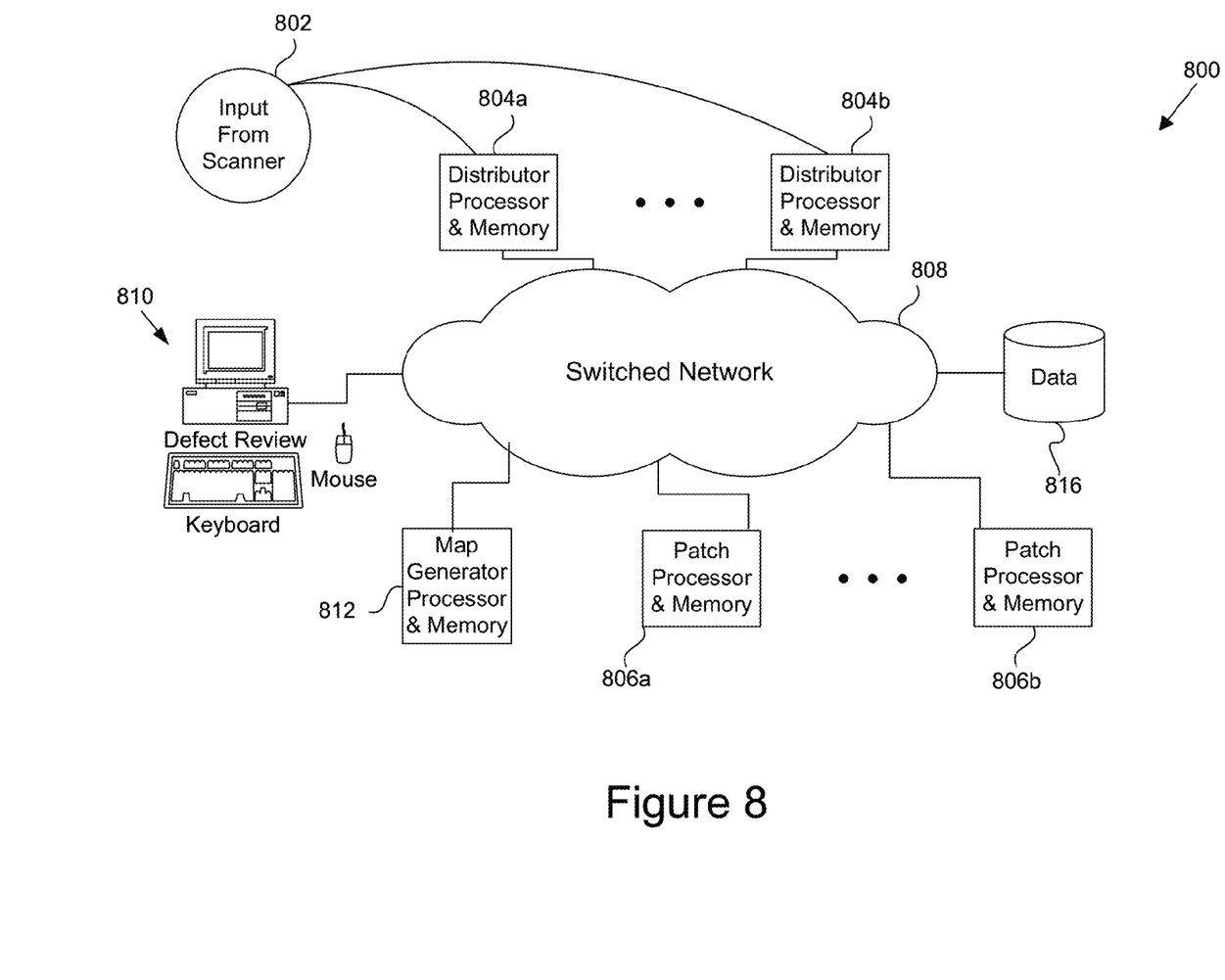
FIG. 8 is a diagrammatic representation of an example inspection system in which techniques of the present invention may be implemented

Techniques of the present invention may be implemented in any suitable combination of hardware and/or software. FIG. 8 is a diagrammatic representation of an example inspection system 800 in which techniques of the present invention may be implemented. The inspection system 800 may receive input 802 from an inspection tool or scanner (not shown). The inspection system may also include a data distribution system (e.g., 804a and 804b) for distributing the received input 802, an intensity signal (or patch) processing system (e.g., patch processors and memory 806a and 806b) for processing specific portions/patches of received input 802, a map generator system (e.g., Map Generator Processor and Memory 812) for generating a combined intensity map, a network (e.g., switched network 808) for allowing communication between the inspection system components, an optional mass storage device 816, and one or more inspection control and/or review stations (e.g., 810) for reviewing the reflected, transmitted, and combined intensity maps. Each processor of the inspection system 800 typically may include one or more microprocessor integrated circuits and may also contain interface and/or memory integrated circuits and may additionally be coupled to one or more shared and/or global memory devices.

The scanner or data acquisition system (not shown) for generating input data 802 may take the form of any suitable instrument (e.g., as described further herein) for obtaining intensity signals or images of a reticle. For example, the scanner may construct an optical image or generate intensity values of a portion of the reticle based on a portion of detected light that is reflected, transmitted, or otherwise directed to one or more light sensors. The scanner may then output the intensity values or image may be output from the scanner.

The scanner or inspection tool may be operable to detect and collect reflected and transmitted light as an incident optical beam scans across each patch of a reticle. As noted above, the incident optical beam may scan across reticle swaths that each comprises a plurality of patches. Light is collected in response to this incident beam from a plurality of points or subareas of each patch.

The scanner or inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. A reflected and transmitted image may be generated after all the positions of the reticle are scanned and converted into detected signals, or potions of a reflected and transmitted image may be generated as each reticle portion is scanned with the final reflected and transmitted image being complete after the entire reticle is scanned.

The detected signals may also take the form of aerial images. That is, an aerial imaging technique may be used to simulate the optical effects of the photolithography system so as to produce an aerial image of the photoresist pattern that is exposed on the wafer. In general, the optics of the photolithography tool are emulated so as to produce an aerial image based on the detected signals from the reticle. The aerial image corresponds to the pattern produced from the light passed through the photolithography optics and reticle onto the photoresist layer of a wafer. Additionally, the photoresist exposure process for the particular type of photoresist material may also be emulated.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

Intensity or image data 802 can be received by data distribution system via network 808. The data distribution system may be associated with one or more memory devices, such as RAM buffers, for holding at least a portion of the received data 802. Preferably, the total memory is large enough to hold an entire swatch of data. For example, one gigabyte of memory works well for a swatch that is 1 million by 1000 pixels or points.

The data distribution system (e.g., 804a and 804b) may also control distribution of portions of the received input data 802 to the processors (e.g. 806a and 806b). For example, data distribution system may route data for a first patch to a first patch processor 806a, and may route data for a second patch to patch processor 806b. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch that is 512 by 1024 pixels. Alternatively, the patch processors may share memory.

Each processor may determine and store average patch intensity values for each set of one or more patches. For instance, each processor may determine an average of one patch or an average for each set of multiple patches. For example, an average may be determined for each set of 1, 2, 50, or 200 patches. The number of patches for which an average is determined, of course, affects the sampling granularity. That is, a higher number of patches for each average calculation is associated with a lower sampling number. However, noise is reduced as more patches are used to determine each average.

Each set of input data 802 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 806a, and the second memory partition may hold and route second data to patch processor 806b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 9A:
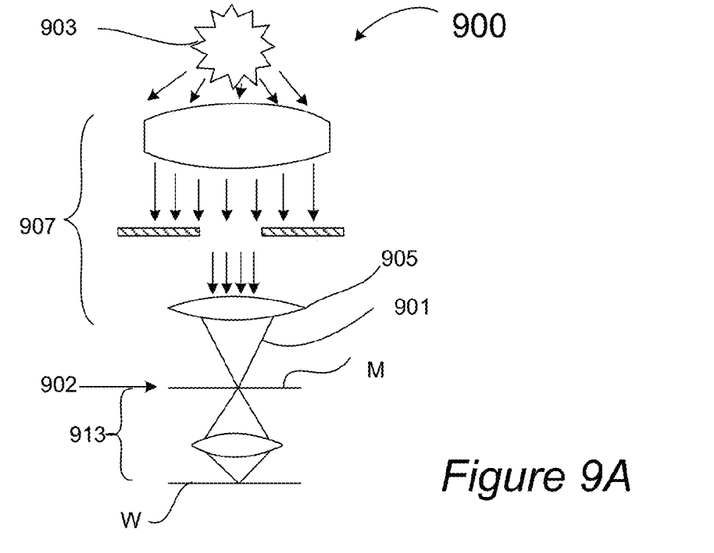
FIG. 9A is a simplified schematic representation of a lithographic system for transferring a mask pattern from a photomask onto a wafer in accordance with certain embodiments.

FIG. 9A is a simplified schematic representation of a typical lithographic system 900 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 903 directs a light beam through an illumination optics 907 (e.g., lens 905) onto a photomask M located in a mask plane 902. Illumination lens 905 has a numeric aperture 901 at that plane 902. The value of the numerical aperture 901 impacts which defects on the photomask are lithographic significant defects and which ones are not. A portion of the beam that passes through the photomask M forms a patterned optical signal that is directed through imaging optics 913 and onto a wafer W to initiate the pattern transfer.

Figure 9B:
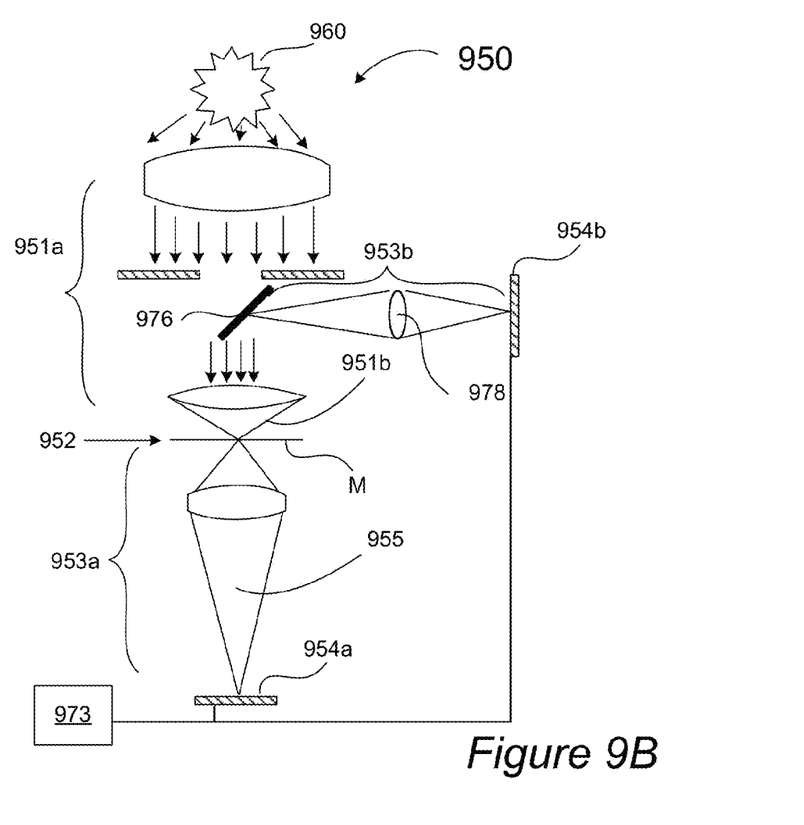
FIG. 9B provides a schematic representation of a photomask inspection apparatus in accordance with certain embodiments.

FIG. 9B provides a schematic representation of an example inspection system 950 that has illumination optics 951a includes an imaging lens with a relative large numerical aperture 951b at a reticle plane 952 in accordance with certain embodiments. The depicted inspection system 950 includes detection optics 953a and 953b, including microscopic magnification optics designed to provide, for example, 60-200× magnification or more for enhanced inspection. For example, numerical aperture 951b at the reticle plane 952 of the inspection system may be considerable greater than the numerical aperture 901 at the reticle plane 902 of the lithography system 900, which would result in differences between test inspection images and actual printed images.

The inspection techniques described herein may be implemented on various specially configured inspection systems, such as the one schematically illustrated in FIG. 9B. The illustrated system 950 includes an illumination source 960 producing a light beam that is directed through illumination optics 951a onto a photomask M in the reticle plane 952. Examples of light sources include a coherent laser light source (e.g., deep UV or gas laser generator), a filtered lamp, LED light source, etc. In one example, the source is a 193 nm laser. As explained above, the inspection system 950 may have a numerical aperture 951b at the reticle plane 952 that may be greater than a reticle plane numerical aperture (e.g., element 901 in FIG. 9A) of the corresponding lithography system. The photomask M to be inspected is placed on a mask stage at the reticle plane 952 and exposed to the source.

The patterned image from the mask M is directed through a collection of optical elements 953a, which project the patterned image onto a sensor 954a. In a reflecting system, optical elements (e.g., beam splitter 976 and detection lens 978) direct and capture the reflected light onto sensor 954b. Although two sensors are shown, a single sensor can be used to detect reflected and transmitted light during different scans of the same reticle area. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 954a and/or 954b) can be processed by a computer system 973 or, more generally, by one or more signal processing devices, which may each include an analog-to-digital converter configured to convert analog signals from each sensor into digital signals for processing. The computer system 973 typically has one or more processors coupled to input/output ports, and one or more memories via appropriate buses or other communication mechanisms.

The computer system 973 may also include one or more input devices (e.g., a keyboard, mouse, joystick) for providing user input, such as changing focus and other inspection recipe parameters. The computer system 973 may also be connected to the stage for controlling, for example, a sample position (e.g., focusing and scanning) and connected to other inspection system components for controlling other inspection parameters and configurations of such inspection system components.

The computer system 973 may be configured (e.g., with programming instructions) to provide a user interface (e.g., a computer screen) for displaying resultant intensity values, images, and other inspection results. The computer system 973 may be configured to analyze intensity, phase, and/or other characteristics of reflected and/or transmitted sensed light beam. The computer system 973 may be configured (e.g., with programming instructions) to provide a user interface (e.g., on a computer screen) for displaying resultant intensity values, images, and other inspection characteristics. In certain embodiments, the computer system 973 is configured to carry out inspection techniques detailed above Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:
defining a plurality of local areas of a reticle;
using an optical reticle inspection tool during an inspection to detect signals in the form of electromagnetic waveforms reflected from a plurality of sub-areas of each local area of the reticle and obtain, for each local area, an average of multiple reflected intensity values corresponding to the detected signals reflected from the plurality of sub-areas of each local area of the reticle;
using the optical reticle inspection tool during the inspection to detect signals in the form of electromagnetic waveforms transmitted through the plurality of sub-areas of each vital of the reticle and obtain, for each local area, an average of multiple transmitted intensity values corresponding to the signals transmitted through the plurality of sub-areas of each local area of the reticle; and
generating and storing or displaying a combined intensity map by combining, for each local area, the average of multiple reflected intensity values and the average of multiple transmitted intensity values such that a reticle pattern of the reticle is cancelled out of the combined intensity map if the reticle has not degraded and such that the reticle pattern of the reticle is not cancelled out of the combined intensity map if the reticle has degraded.

2. The method of claim 1; wherein the combined intensity map indicates that the reticle has degraded in a spatially radial pattern that results in the combined intensity map comprising a plurality of intensity values, which correspond to both a reticle pattern portion and a spatially radial pattern of degradation on the reticle, that differs from a plurality of intensity values, which correspond to portions of the reticle that are outside the reticle pattern portion.

3. The method of claim 2, wherein the inspection is performed after the reticle is used repeatedly in a photolithography process and the spatially radial pattern is caused by the photolithography process.

4. The method of claim 1, wherein the average of multiple reflected intensity values and the average of multiple transmitted intensity values are combined so that the combined intensity map comprises a plurality of intensity values, which correspond to pattern portions on the reticle, that are substantially equal to a plurality of intensity values, which correspond to non-pattern portions on the reticle, when there is no degradation on such reticle.

5. The method of claim 1, wherein the average of multiple reflected intensity values for each local area is obtained from the detected reflected intensity image obtained by the optical reticle inspection tool and the average of multiple transmitted intensity values for each local area is obtained from the detected transmitted intensity image obtained by the optical reticle inspection tool, and wherein the combined intensity map is in the form of an image that combines both the reflected and transmitted intensity images.

6. The method of claim 5, wherein each local region corresponds to a pixel of the detected reflected and transmitted intensity image.

7. The method of claim 5, wherein each local region corresponds to a patch of the detected reflected and transmitted intensity image, wherein each patch has a plurality of pixels.

8. The method of claim 1, wherein the average of multiple reflected intensity values and the average of multiple transmitted intensity values are combined by weighting particular values from the multiple reflected and transmitted intensity values.

9. The method of claim 1, wherein the plurality of local areas substantially comprises the entire active area of the reticle and the combined intensity map is generated for the entire active area of the reticle.

10. The method of claim 1, wherein the inspection is performed while a pellicle is mounted on the reticle and the combined intensity map indicates whether a pellicle of the reticle has degraded over time more than a predefined level.

11. The method of claim 1, further comprising analyzing the combined intensity map to determine whether the reticle has degraded.

12. An inspection system for inspecting a photolithographic reticle, the system comprising:
a light source for generating an incident beam;
an illumination optics module for directing the incident beam onto a sample;
a collection optics module for directing a reflected output beam, which is reflected from the sample in response to the incident beam; and a transmitted output beam, which is transmitted through the sample in response to the incident beam, to at least one sensor;
at least one sensor for detecting the reflected output beam and generating a reflected intensity image or signal for the reflected output beam and detecting the transmitted output beam and generating a transmitted intensity image or signal for the transmitted output beam; and
a controller that is configured to perform the following operations:
defining a plurality of local areas of a reticle;
for each local area and during an inspection, obtaining from the detected reflected intensity image or signal an average of multiple reflected intensity values corresponding to the reflected output beam reflected from a plurality of sub-areas of each local area of the reticle;
for each local area and during the inspection, obtaining from the detected transmitted intensity image or signal an average of multiple transmitted intensity values corresponding to the transmitted output beam transmitted through the plurality of sub-areas of each local area of the reticle; and
generating and storing or displaying a combined intensity map by combining, for each local area, the average of multiple reflected intensity values and the average of multiple transmitted intensity values such that a reticle pattern of the reticle is cancelled out of the combined intensity map if the reticle has not degraded and such that the reticle pattern of the reticle is not cancelled out of the combined intensity map if the reticle has degraded.

13. The system of claim 12, wherein the combined intensity map indicates that the reticle has degraded in a spatially radial pattern that results in the combined intensity map comprising a plurality of intensity values, which correspond to both a reticle pattern portion and a spatially radial pattern of degradation on the reticle, that differs from a plurality of intensity values, which correspond to portions of the reticle that are outside the reticle pattern portion.

14. The system of claim 13, wherein the inspection is performed after the reticle is used repeatedly in a photolithography process and the spatially radial pattern is caused by the photolithography process.

15. The system of claim 12, wherein the average of multiple reflected intensity values and the average of multiple transmitted intensity values are combined so that the combined intensity map comprises a plurality of intensity values, which correspond to pattern portions on the reticle, that are substantially equal to a plurality of intensity values, which correspond to non-pattern portions on the reticle, when there is no degradation on such reticle.

16. The system of claim 12, wherein the average of multiple reflected intensity values for each local area is obtained from the detected reflected intensity image obtained from the reflected output beam and the average of multiple transmitted intensity values for each local area is obtained from the detected transmitted intensity image obtained from the transmitted output beam, and wherein the combined intensity map is in the form of an image that combines both the reflected and transmitted intensity images.

17. The system of claim 16, wherein each local region corresponds to a pixel of the detected reflected and transmitted intensity image.

18. The system of claim 16, wherein each local region corresponds to a patch of the detected reflected and transmitted intensity image, wherein each patch has a plurality of pixels.

19. The system of claim 12, wherein the average of multiple reflected intensity values and the average of multiple transmitted intensity values are combined by weighting particular values from the multiple reflected and transmitted intensity values.

20. The system of claim 12, wherein the plurality of local areas substantially comprises the entire active area of the reticle and the combined intensity map is generated for the entire active area of the reticle.

21. The system of claim 12, wherein the inspection is performed while a pellicle is mounted on the reticle and the combined intensity map indicates whether a pellicle of the reticle has degraded over time more than a predefined level.

22. The system of claim 12, wherein the controller is further configured to analyze the combined intensity map to determine whether the reticle has degraded.

* * * * *